US012588884B2

(12) United States Patent
Nandi et al.

(10) Patent No.: US 12,588,884 B2
(45) Date of Patent: Mar. 31, 2026

(54) CLOSED-LOOP ELUTION SYSTEM TO EVALUATE PATIENTS WITH SUSPECTED OR EXISTING PERIPHERAL ARTERIAL DISEASE

(71) Applicants: Jubilant Draximage Inc., Montreal (CA); Indranil Nandi, Yardley, PA (US)

(72) Inventors: Indranil Nandi, Yardley, PA (US); Anita Jolene MacDonald, Kirkland (CA); Norman LaFrance, Yardley, PA (US); Tanima Ghosh, Kirkland (CA)

(73) Assignee: Jubilant Draximage Inc. (CA)

( * ) Notice: Subject to any disclaimer, the term of this patent is extended or adjusted under 35 U.S.C. 154(b) by 44 days.

(21) Appl. No.: 18/563,095

(22) PCT Filed: Jun. 10, 2022

(86) PCT No.: PCT/US2022/033109

§ 371 (c)(1),
(2) Date: Nov. 21, 2023

(87) PCT Pub. No.: WO2022/261501

PCT Pub. Date: Dec. 15, 2022

(65) Prior Publication Data

US 2024/0225579 A1      Jul. 11, 2024

Related U.S. Application Data

(60) Provisional application No. 63/209,495, filed on Jun. 11, 2021.

(51) Int. Cl.
*A61B 6/50*          (2024.01)
*A61B 6/00*          (2024.01)
(Continued)

(52) U.S. Cl.
CPC .............. *A61B 6/504* (2013.01); *A61B 6/037* (2013.01); *A61B 6/481* (2013.01); *A61B 6/5217* (2013.01); *A61K 51/04* (2013.01)

(58) Field of Classification Search
CPC ......... A61B 6/504; A61B 6/037; A61B 6/481; A61B 6/5217; A61B 5/055; A61B 5/4836;
(Continued)

(56) References Cited

U.S. PATENT DOCUMENTS

2008/0128626 A1*  6/2008  Rousso ................ A61B 6/4258
                                                                250/362
2010/0179422 A1      7/2010  O'Conner
(Continued)

OTHER PUBLICATIONS

Stacy et al. 2020 in Imaging in Peripheral Arterial Disease, Kramer Edt, Springer Nature Switzerland 2020, Chapt. 11:195-215 (Year: 2020).*
(Continued)

*Primary Examiner* — Keith M Raymond
*Assistant Examiner* — Patrick M Mehl
(74) *Attorney, Agent, or Firm* — William D. Hare; McNeely, Hare & War, LLP

(57)          ABSTRACT

The present invention provides a closed loop generation and/or infusion system comprising a radionuclide generator, an activity detector, a controller, a dose calibrator, a pump, eluant source and an automated elution system controlled by software and hardware for generation and infusion of a radionuclide for administering a dose of generated radionuclide into a subject for diagnosing a peripheral arterial disease in a subject suffering from or suspected of suffering from peripheral arterial disease and/or metabolic disease via Positron Emitting Tomography (PET) or Single-photon emission computed tomography (SPECT) imaging technologies. More particularly, the present invention provides
(Continued)

methods of determining whether a subject is suffering or at a risk of developing a peripheral arterial disease by performing quantitative assessment of blood flow in lower extremities or limbs of the subject; wherein the quantitative assessment is performed by analyzing one or more images and providing a severity score; and wherein the analysis of the one or more images is performed by using an automated system.

18 Claims, 5 Drawing Sheets

(51) Int. Cl.
 *A61B 6/03* (2006.01)
 *A61K 51/04* (2006.01)

(58) Field of Classification Search
 CPC ... A61B 5/4842; A61B 5/7267; A61B 5/7275; A61B 2576/00; A61B 5/02007; A61B 5/02755; A61K 51/04; A61K 33/00; G16H 15/00; G16H 20/10; G16H 20/30; G16H 20/40; G16H 20/60; G16H 20/70; G16H 30/20; G16H 30/40; G16H 40/67; G16H 50/20; G16H 50/30; G16H 50/70; G16H 80/00; A61P 9/10
 See application file for complete search history.

(56) References Cited

U.S. PATENT DOCUMENTS

| | | | |
|---|---|---|---|
| 2014/0119621 A1 | 5/2014 | Uber | |
| 2014/0374615 A1* | 12/2014 | Hidem | ................... G16Z 99/00 |
| | | | 250/393 |
| 2020/0312474 A1 | 10/2020 | Lefort et al. | |

OTHER PUBLICATIONS

Theiss et al. 1996 Vascular Surgery 30:331-336 (Year: 1996).*
Senthamizhchelvan et al. 2010 J. Nucl. Med. 51:1582-1599 (Year: 2010).*
Sicurello (2020. Medical informatics and telemedicine: 50 Years of developments online https://www.iiimb.me/files/3-6-5-20--telemedicine-Sicurello--50-years.pdf (Year: 2020).*
International Search Report and Written Opinion, PCT/US2022/033109, Oct. 27, 2022.

* cited by examiner

CLOSED-LOOP ELUTION SYSTEM TO EVALUATE PATIENTS WITH SUSPECTED OR EXISTING PERIPHERAL ARTERIAL DISEASE

TECHNICAL FIELD

The present invention relates in general to nuclear imaging and medicine, in particular, to Positron Emitting Tomography (PET) for diagnosing and/or treating peripheral arterial disease.

BACKGROUND

Peripheral arterial disease (PAD) is a progressive atherosclerotic disease of the lower limbs affecting large populations in the world and advances more quickly in patients with metabolic disease like diabetes mellitus (DM), which remains a major health care issue across the world. Microvascular disease is highly prevalent in DM patients, which further complicates the evaluation and treatment of peripheral arterial disease in diabetic patients that suffer from disease of both the large vessels and microcirculation.

The various conventional methods of diagnosing peripheral arterial disease include: a) physical examination, b) Ankle-brachial index (ABI), c) Duplex ultrasonography, d) CT/CMR, an invasive angiography, and e) blood tests. These tests have several disadvantages such as unable to specify exact lesion locations; can only evaluate major blood vessels; and lacks of quantitative tools to access the physiologic consequences. None of these tests provides quantitative assessment of the blood flow in the affected part of a subject suffering from peripheral arterial disease with or without diabetes mellitus.

PET agents like $^{18}$F-FDG known for atherosclerosis has a disadvantage especially in diabetic patients wherein administration of FDG can further increase the blood glucose levels and can cause problems for patient suffering from diabetes mellitus. It is known that $^{18}$F-FDG uptake is altered in patients with diabetes mellitus; therefore, diabetic patients may need stabilization of blood glucose on the day preceding, and on the day of the $^{18}$F-FDG scan. Therefore, there exists an unmet and urgent need to identify a suitable PET tracer for diagnosis of peripheral arterial disease in subjects suffering from a metabolic disease like diabetes mellitus.

There also exists an unmet urgent need to identify a suitable PET tracer, imaging protocol, method of administering a PET tracer, radioisotope generation/elution and infusion system, elution protocol, method of diagnosing and identifying the patients at risk of developing peripheral arterial disease, artificial intelligence-based image analysis and suggesting therapy options for diagnosis and/or treatment of peripheral arterial disease in subjects.

SUMMARY

The present invention relates to novel non-invasive method of diagnosing and/or treating Peripheral Arterial Disease (PAD) in a subject.

It is an object of the present disclosure to provide non-invasive method of diagnosing and/or treating peripheral arterial disease in a subject.

It is an object of the present disclosure to provide non-invasive method of diagnosing and/or treating peripheral arterial disease in a subject suffering from diabetes mellitus.

It is an object of the present disclosure to provide non-invasive imaging of a body part or region of interest (ROI)

for diagnosing and/or treating peripheral arterial disease in a subject suffering from diabetes mellitus.

It is an object of the present disclosure to provide a method of non-invasive imaging of a body part or region of interest for diagnosing and/or treating peripheral arterial disease in a subject suffering from diabetes mellitus comprising administering a Positron Emission Tomography (PET) agent and imaging the region of interest.

It is an object of the present disclosure to provide a method of non-invasive imaging of a body part or region of interest for diagnosing and/or treating peripheral arterial disease in a subject suffering from diabetes mellitus comprising administering a Positron Emission Tomography (PET) agent using closed loop elution system.

It is an object of the present disclosure to provide a method of non-invasive imaging of a body part or region of interest for diagnosing and/or treating peripheral arterial disease in a subject suffering from diabetes mellitus comprising administering a dose of Rb-82 and imaging a region of interest using closed loop Rb-82 elution system.

It is an object of the present disclosure to provide non-invasive imaging of a body part or region of interest for identifying a risk of developing peripheral arterial disease in a subject suffering from diabetes mellitus comprising administering Rb-82 using a closed loop Rb-82 elution system and imaging a region of interest.

It is an object of the present disclosure to diagnose and/or treat a subject suffering from or at a risk of developing peripheral arterial disease comprising administering a dose of Rb-82 using a closed loop Rb-82 elution system and performing a quantitative assessment of blood flow to the region of interest.

It is an object of the present disclosure to provide a novel imaging approach and/or protocol for diagnosis of peripheral arterial disease in a subject suffering from diabetes mellitus.

It is an object of the present disclosure to provide a novel imaging approach and/or protocol for diagnosis of limb ischemia in a subject.

It is an object of the present disclosure to provide a novel imaging approach and/or protocol for diagnosis of limb ischemia in a subject suffering from diabetes mellitus.

It is an object of the present disclosure to provide a novel imaging approach and/or protocol for identifying a subject at a risk of developing limb ischemia.

It is an object of the present disclosure to provide a novel imaging approach and/or protocol for the quantitative evaluation of peripheral arterial disease in a subject suffering from diabetes mellitus.

It is an object of the present disclosure to provide a novel imaging approach and/or protocol for the quantitative evaluation of lower extremity perfusion at rest and stress for application in patients suspected of peripheral arterial disease.

It is an object of the present disclosure to provide a novel imaging approach and/or protocol for the quantitative evaluation of lower extremity perfusion at rest and stress.

It is an object of the present disclosure to provide automated infusion of an imaging agent into a subject for diagnosing peripheral arterial disease in a subject.

It is an object of the present disclosure to provide pharmaceutical compositions and kits for imaging agent in an injectable dosage form.

It is an object of the present invention to provide the severity score of disease based on the quantitative assessment of peripheral arterial disease in a subject.

It is an object of the present disclosure to provide automated image analysis based on algorithms, artificial intelligence, machine learning, or artificial neural network or simulated neural network (SNN) and/or deep learning neural network and provide the severity score based on the assessment.

It is an object of the present disclosure to provide artificial intelligence technique for image analysis, decision support to classify severity with suggested treatment options.

It is an object of the present disclosure to provide therapy options based on the severity score.

It is an object of the present invention to provide an all-in-one integrated hardware/software apparatus providing a quantitative, non-invasive, personalized assessment method to measure blood perfusion in lower extremities using a closed-loop Rb-82 chloride injection delivery system, integrated hardware/software apparatus, as a total system for detection, diagnosis of severity, consultation, therapy and follow-up rehabilitation of patients with peripheral arterial disease. This non-invasive approach will provide a quantitative assessment of lower extremities perfusion at rest, along with perfusion reserve in response to pharmacological stress/exercise based stress.

It is an object of the present disclosure to provide a scanning technique for lower extremities; software and hardware based Rb-82 chloride delivery methods and protocol to reliably detect and diagnose peripheral arterial disease; an expert system to score the peripheral arterial disease severity, decision support tools for clinical outcomes, such as baseline score, survival rate after diagnosis and local disease progression rate; and a telemedicine portal for patient follow-up.

It is a further objective of the present invention to provide a quantifiable prediction tool based on flow rate measurements, serial imaging with repeated Rb-82 chloride injections and scanning method of lower extremities independent of the scanner/camera type.

It is an object of the present disclosure to provide a method of carrying out a non-invasive personalized screening test for peripheral arterial disease.

It is an object of the present disclosure to provide a definitive, reliable diagnostic test during first line investigation to assess symptoms attributable to peripheral arterial disease in adults with diabetes.

The present invention concerns any of the following aspects:

In one aspect of the present invention, a closed loop generation and/or infusion system comprising a radionuclide generator, an activity detector, a controller, a dose calibrator, a pump, eluant source and software for generation and infusion of a radionuclide for administering a dose of generated radionuclide into the subject for diagnosing a peripheral arterial disease in a subject suffering from or suspected of suffering from peripheral arterial disease and metabolic disease.

In another aspect of the present invention, the radionuclide generator comprises $^{99}Mo/^{99m}Tc$, $^{90}Sr/^{90}Y$, $^{82}Sr/^{82}Rb$, $^{188}W/^{188}Re$, $^{68}Ge/^{68}Ga$ $^{42}$ $Ar/^{42}K$, $^{44}Ti/^{44}Sc$, $^{52}Fe/^{52m}Mn$, $^{72}Se/^{72}$ As, $^{83}Rb/^{83m}Kr$; $^{103}Pd/^{103m}Rh$, $^{109}Cd/^{109m}$ Ag, $^{113}Sn/^{113m}$ In, $^{118}Te/^{118}Sb$, $^{132}Te/^{132}I$, $^{137}Cs/^{137m}Ba$, $^{140}Ba/^{140}La$, $^{134}Ce/^{134}La$, $^{144}Ce/^{144}Pr$, $^{140}Nd/^{140}Pr$, $^{166}Dy/^{166}Ho$, $^{167}Tm/^{167m}Er$, $^{172}Hf/^{172}Lu$, $^{178}W/^{178}Ta$, $^{191}Os/^{191m}Ir$, $^{194}Os/^{194}Tr$, $^{226}Ra/^{222}Rn$ and $^{225}$ $Ac/^{213}Bi$.

In another aspect of the present invention, the generation comprises elution of daughter isotope from parent isotope bound to generator column by suitable eluant.

In another aspect of the present invention, the radionuclide generator comprises $^{82}Sr/^{82}Rb$ generator.

In another aspect of the present invention, the system is automated.

In another aspect of the present invention, the radionuclide comprises Rb-82.

In another aspect of the present invention, the dose of radionuclide is automatically calculated based on subject parameters, radionuclide generation and infusion system parameters, imaging system parameters.

In another aspect of the present invention, the subject parameters comprise subject weight, height, sex, age, ongoing medications, allergies, radiation sensitivity, body mass, surface area, kidney and liver function status or combination thereof.

In another aspect of the present invention, the radionuclide generation and infusion system parameters comprises type of radionuclide, generator type, generator age, flow rate, activity to be administered, infusion time, dose, activity detector calibration, parent isotope breakthrough.

In another aspect of the present invention, the imaging system parameters comprise scanner resolution, scanner sensitivity and type of camera or combination thereof.

In another aspect of the present invention, the parent isotope comprises Sr-82 and daughter isotope comprises Rb-82.

In another aspect of the present invention, the elution mode comprises constant activity, constant flow, constant pressure, constant infusion time, and constant dose or combinations thereof.

In another aspect of the present invention, the closed loop elution system, the dose is fixed dosing or linear dosing based on subject weight or body mass.

In another aspect of the present invention, the system is communicatively or electronically coupled to imaging system.

In another aspect of the present invention, the imaging system comprises PET or SPECT imaging systems.

In another aspect of the present invention, the dose of radionuclide ranges from 0.01 mBq to 10,000 mBq.

In another aspect of the present invention, the metabolic disease is diabetes mellitus.

In another aspect of the present invention, the peripheral arterial disease comprises limb ischemia.

In yet another aspect of present invention, a method of diagnosing a peripheral arterial disease in a subject suffering from diabetes mellitus comprises: a) calculating a dose of Rb-82 based on subject parameters, imaging system parameters, generation and/or infusion system parameters; b) administering the calculated dose of Rb-82 to a subject in at rest and stress conditions; c) image capturing by PET scanner; d) performing quantitative assessment of blood flow in lower extremities or limbs of the subject; e) performing image analysis and providing a severity score based on the assessment, the severity score may be represented in numerical values or percentage occlusion; f) performing diagnosis or identify the subjects at risk of developing peripheral arterial disease; and g) generating the report.

In another aspect of the present invention, the method of diagnosing a peripheral arterial disease in a subject suffering from diabetes mellitus, further comprises a telemedicine portal for follow-up, therapy adjustment, rehabilitation of the subject.

In another aspect of the present invention, the method of diagnosing a peripheral arterial disease in a subject suffering from diabetes mellitus, further comprises a secure databank of subject parameters, images for Rb-82 dose calculation, image analysis, diagnosis and rehabilitation of subject.

DESCRIPTION

Figure 1:
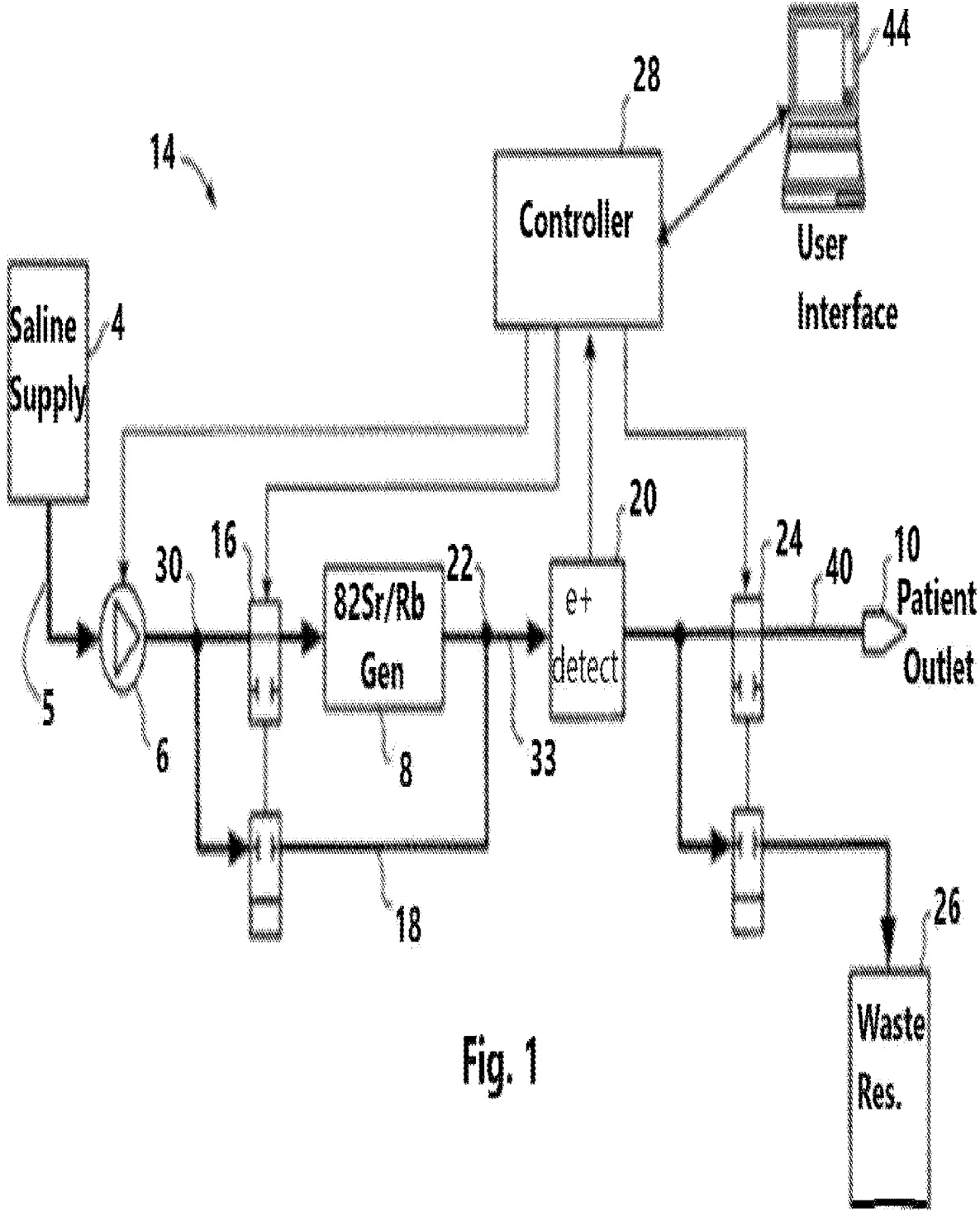
FIG. 1: Depicts a diagram schematically demonstrating principal elements of an automated Rb-82 generation and infusion system in accordance with an embodiment of the present invention.

There is currently a need to diagnose and treat peripheral arterial disease in subjects suspected or afflicted with the disease. The subjects can be suffering from accompanying conditions like metabolic diseases. The unexpected discovery further provides an accurate quantitative assessment of the blood perfusion or blood flow to the affected area or the region of interest.

The present invention can be more readily understood by reading the following detailed description of the invention and included embodiments.

As used herein, the term 'Peripheral Arterial Disease' (PAD) refers to a circulatory problem in which narrowed arteries reduce blood flow to limbs or other part of body. Peripheral arterial disease is a disease of the blood vessels located outside the heart and brain and most often caused by a buildup of fatty deposits in the arteries. PAD affects the blood vessels causing them to narrow, therefore restricting the blood flow to the arms, kidneys, stomach, and most commonly, the legs. Peripheral artery disease is a major risk factor for heart attack and stroke. Possible symptoms of peripheral arterial disease include one or more of hair loss on the feet and legs, intermittent claudication, pain in the thigh or calf muscles, leg weakness, cold feeling in foot or leg, numbness, brittle toenails, slow growth of toenails, sores or ulcers on the legs and feet that take a long time to heal, skin on the legs becomes shiny or turns pale or bluish, and erectile dysfunction. The most common cause of PAD is atherosclerosis. Atherosclerosis is a steady process in which a fatty material builds up inside the arteries. Less common causes of peripheral artery disease are blood clots in the arteries, injury to the limbs. Risk factors that contribute to PAD are diabetes, smoking, obesity, high blood pressure, increasing age, high cholesterol, family history of heart disease, and excess levels of C-reactive protein or homocysteine. Undiagnosed or untreated PAD can be dangerous; it can lead to painful symptoms, loss of limbs, increased risk of coronary artery disease, and carotid atherosclerosis (a narrowing of the arteries that supply blood to the brain). As people with PAD have an increased risk of heart attack and stroke, the American Heart Association encourages people at risk to discuss PAD with their doctor to ensure early diagnosis and treatment.

As used herein, the term 'metabolic disease' refers to a cluster of conditions that occur together, increasing risk of heart disease, stroke and type 2 diabetes. These conditions include increased blood pressure, diabetes mellitus, excess body fat around the waist, and abnormal cholesterol or triglyceride levels.

As used herein, the term 'diabetes mellitus' refers to a group of metabolic disorders characterized by a high blood sugar level over a prolonged period of time. Symptoms often include frequent urination, increased thirst and increased appetite. If left untreated, diabetes can cause many health complications. Acute complications can include diabetic ketoacidosis, hyperosmolar hyperglycemic state, or death. Serious long-term complications include cardiovascular disease, stroke, chronic kidney disease, foot ulcers, damage to the nerves, damage to the eyes and cognitive impairment. Diabetes occurs due to either the pancreas not producing enough insulin, or the cells of the body not responding properly to the insulin produced. There are three main types of diabetes: Type 1 diabetes results from failure of the pancreas to produce enough insulin due to loss of beta cells. This form was previously referred to as "insulin-dependent diabetes mellitus" (IDDM) or "juvenile diabetes". The loss of beta cells caused by an autoimmune response wherein the cause of autoimmune response is unknown. Type 2 diabetes begins with insulin resistance, a condition in which cells fail to respond to insulin properly. As the disease progresses, a lack of insulin can also develop. This form was previously referred to as "non-insulin-dependent diabetes mellitus" (NIDDM) or "adult-onset diabetes". The most common cause is a combination of excessive body weight and insufficient exercise. Gestational diabetes is the third main form, and occurs when pregnant women without a previous history of diabetes develop high blood sugar levels.

As used herein, the term 'diagnosis' refers to a process of identifying a disease, condition, or injury from its signs and symptoms.

As used herein, the term 'imaging' refers to techniques and processes used to create images of various parts of the human body for diagnostic and treatment purposes within digital health. Examples of imaging include: X-ray radiography, Fluoroscopy, Magnetic resonance imaging (MRI), Computed Tomography (CT), Medical ultrasonography or ultrasound Endoscopy Elastography, Tactile imaging, Thermography Medical photography, and nuclear medicine functional imaging techniques, e.g., positron emission tomography (PET) or SPECT (Single-photon emission computed tomography). Imaging seeks to reveal internal structures, as well as to diagnose and treat disease.

As used herein, the term 'Positron Emission Tomography' (PET) refers to a functional imaging technique that uses radioactive substances known as radiotracers or radionuclides to visualize and measure changes in metabolic processes, and in other physiological activities including blood flow, regional chemical composition, and absorption. Different tracers are used for various imaging purposes, depending on the target process within the body commonly used radionuclide tracers for PET imaging include Rb-82 (Rubidium-82), 0-15 (Oxygen-15), F-18 (Fluorine-18), Ga-68 (Gallium-68), Cu-61 (Copper-61), C-11 (Carbon-11), N-13 (Ammonia-13), Co-55 (Cobalt-55), Zr-89 (Zirconium-89). The preferred radionuclide comprises Rb-82 having a half-life of about 76 seconds.

As used herein, the term 'SPECT' refers to a Single-photon emission computed tomography is a nuclear medicine tomographic imaging technique using gamma rays. The SPECT technique is able to provide three-dimensional (3D)

information. The technique needs delivery of a gamma-emitting radioisotope (a radionuclide) into the patient, normally through injection into the bloodstream. A radioisotope can be attached to a specific ligand to create a radioligand, whose properties bind it to certain types of tissues. This allows the combination of ligand and radiopharmaceutical to be carried and bound to a region of interest in the body, where the ligand concentration assessed by a gamma camera. SPECT agents include $^{99}$mTc, $^{123}$I, $^{131}$I, $^{111}$In, $^{155}$Tb and $^{133}$Xe.

As used herein, the term 'Computed Tomography (CT)' refers to a computerized x-ray imaging in which a beam of x-rays is aimed at a patient and rotated around the body, producing signals that are processed by the machine's computer to generate cross-sectional images of the body. These slices are called tomographic images and contain detailed information than conventional x-rays. Once the machine's computer collects a number of successive slices, they can be digitally "stacked" together to form a three-dimensional image of the patient that allows for easier identification and location of basic structures as well as possible tumors or abnormalities.

As used herein, the term 'Magnetic Resonance Imaging (MRI)' is a non-invasive imaging technology that produces 3D detailed anatomical images, which is used for disease detection, diagnosis, and treatment monitoring. MRI is based on technology that excites and detects the change in the direction of the rotational axis of protons found in the water that makes up living tissues.

As used herein, the term 'closed loop generation and infusion system' refers to system for generation and/or infusion of a radionuclide or radiotracer and administration into a subject. The automated infusion system comprises radioisotope generator, dose calibrator, computer, controller, display device, activity detector, cabinet, cart, waste bottle, sensors, shielding assembly, alarms or alerts mechanism, tubing, source vial, diluent or eluant, valves. The automated infusion system can be communicatively or electronically coupled to imaging system.

As used herein, the term 'elution' refers to eluting daughter isotope from parent isotope bound to column using suitable eluant.

As used herein, the term 'constant activity elution mode' refers to elution wherein activity is constant and other parameters of the system may vary.

As used herein, the term 'constant time' refers to elution wherein time of infusion or elution is constant and other parameters of the system may vary.

As used herein, the term 'constant flow' refers to elution wherein eluant flow is constant and other parameters of the system may vary.

As used herein, the term 'constant pressure' refers to elution wherein system pressure is constant and other parameters of the system may vary.

As used herein, the term "generator system" or "generator" or "radioisotope generator" refers to one or more columns containing radioisotope in a shielded container wherein a radiation shielding material surrounds the columns in order to absorb the energy radiating from the generator container, thus protecting the end user from getting exposed to harmful radiation.

As used herein, the term "Sr/Rb elution system" or "$^{82}$Sr/$^{82}$Rb elution system" refers to infusion system meant for generating a solution containing $^{82}$Rb, measuring the radioactivity in the solution, and infusing the solution into a patient in order to perform various studies for diagnosing peripheral arterial disease in a subject.

As used herein, the term "eluant" refers to the liquid or the fluid used for selectively leaching out the daughter radioisotopes from the generator column.

As used herein, the term "eluate" refers to the radioactive eluant after acquisition of daughter radioisotope from the generator column.

As used herein, the term "quality control test" refers to the tests performed on a daily basis for evaluating the safety and efficacy of elution system and more precisely the generator system. If any of the quality control tests fail, then the generator system is configured to not perform a patient elution. The quality control measures may include, but are not limited to, checking and/or testing the status of each of the columns, breakthrough testing on at least one column, flow rate, leakage, column and tubing pressure, eluant volume, waste bottle volume, eluate reservoir volume, activity of parent and daughter isotopes, sensors, pump and valves functioning, checking the environment surrounding elution system, testing outputs produced by each of the columns, and/or performing testing on samples of the radiopharmaceuticals produced by columns, among other quality control measures. The quality control system may be used to generate one or more quality reports relating to the quality of the radiopharmaceuticals produced by the elution system. Quality reports may include, but are not limited to: analytical tests performed on the product; total yield of the products; failure reports for the product; failure reports for the one or more systems used to manufacture the product; and/or operator error reports, among other quality reports. The quality control system may interface with each individual system when performing the quality control tests.

In an embodiment of the invention, the elution system further comprises a stress agent source. In an embodiment, the stress agent infusion is performed at a predetermined time prior to infusing the daughter radioisotope eluate to the patient. In an embodiment, said predetermined time is dependent on the nature of the stress agent.

As used herein, the term 'assessment' refers to a qualitative or quantitative assessment of the blood perfusion in a body part or region of interest. The assessment can be based on artificial intelligence-based algorithms or software.

As used herein the term "severity score" assessment in peripheral arterial disease (PAD) of a person is considered to have peripheral arterial disease when the ankle brachial index (ABI) or ankle brachial pressure index (ABPI) is less than equal to 0.90, however, PAD can be further graded as mild to moderate if the ABI is between 0.41 and 0.90, and severe if an ABI is less than 0.40.

As used herein, the term 'non-invasive' refers to, when no tools enter the body of the subject.

As used herein, the term 'stress agent' refers to agents used to generate stress in a patient or a subject during imaging procedure. The stress agents according to the present invention are selected from regadenoson, dobutamine, adenosine, and dipyridamole. Alternatively, stress can be induced by exercise without use of a stress agent depending on the subject's condition.

As used herein, the term 'dose' refers to the dose of radionuclide required to perform imaging in a subject. The dose of a radionuclide to be administered into the subject ranges from 0.01 mBq to 10,000 mBq. The dose can be fixed or can be calculated based on subject body weight, mass, height, age or infusion system parameters like infusion time, infusion rate, imaging scanner sensitivity, type of radionuclide, imaging scanner/camera resolution, radionuclide generator age, or on-going medications, body organs (like liver, kidney) function status, allergies or combinations thereof by the automated generation or infusion system.

As used herein, the term 'artificial intelligence (AI)' refers to the simulation of human intelligence in machines that are programmed to think like humans and mimic their actions. The term can also be applied to any machine that exhibits traits associated with a human mind such as learning and problem solving. A subset of artificial intelligence is machine learning, which refers to the concept that computer programs can automatically learn from and adapt to new data without being assisted by humans. Deep learning techniques enable this automatic learning through the absorption of huge amounts of unstructured data such as text, images, or video. The automated image analysis is based on algorithms, artificial intelligence, machine learning, or artificial neural network or simulated neural network (SNN) and/or deep learning neural network, which provide the severity score based on the assessment.

As used herein the term 'region of interest (ROI)' refers the samples within a data set identified for a particular purpose. In computer vision and optical character recognition, the ROI defines the borders of an object under consideration. A ROI is a form of annotation, often associated with categorical or quantitative information, expressed in text or in a structured form. It is a portion of an image that can be filtered or operated on in some way.

As used herein, the term 'telemedicine' refers to the practice of caring for patients remotely when the provider and patient are not physically present.

As used herein, "predetermined threshold value" refers to a threshold value of blood perfusion in normal subjects.

In an embodiment, the present invention provides a method of diagnosing peripheral arterial disease in a subject comprising performing a PET scan, PET/CT scan, SPECT scan, PET/MRI scan, MRI scan or combinations thereof by administering a PET agent, SPECT agent, contrast agent, dye or combinations thereof.

In an embodiment according to the present invention, peripheral arterial disease comprises limb ischemia, plaque formation, atherosclerosis, inhibited or decreased blood perfusion or blood flow to any body part, preferably limbs.

In an embodiment, the present invention provides the imaging protocols for diagnosing a peripheral arterial disease in a subject. Imaging protocols are based on PET, SPECT CT, MRI or combinations thereof.

In an embodiment, the radionuclide is selected from a PET or SPECT agent. The PET or SPECT agent can be radiolabeled with one or more ligands or can be administered without radiolabeling.

In another embodiment, the radionuclide is attached to the ligand before administration into the subject. The ligands are provided in suitable dosage form and radionuclide is attached to the ligand and then administered into the subject for imaging. The ligands according to the present invention can be selected from Tetrofosmin, Sestamibi, and Fluorodeoxyglucose.

In an embodiment, PET agents can be selected from Rb-82 (Rubidium-82), O-15 (Oxygen-15), F-18 (Fluorine-18), Ga-68 (Gallium-68), Cu-61 (Copper-61), C-11 (Carbon-11), N-13 (Ammonia-13), Co-55 (Cobalt-55), and Zr-89 (Zirconium-89).

In an embodiment, SPECT agents can be selected from $^{99}$mTc. $^{123}$I, $^{131}$I, $^{111}$In $^{155}$Tb, $^{201}$Tl and $^{133}$ Xe.

In an embodiment, the present invention provides a closed loop generation and/or infusion system comprising a radionuclide generator, an activity detector, a controller, a dose calibrator, a pump, eluant source and an automated elution system controlled by software and hardware for generation and infusion of a radionuclide for administering a dose of generated radionuclide into a subject for diagnosing a peripheral arterial disease in a subject suffering from or suspected of suffering from peripheral arterial disease and/or metabolic disease by performing quantitative assessment of blood flow in lower extremities or limbs of the subject; wherein the quantitative assessment is performed by analyzing one or more images and/or blood flow measurements and providing a severity score; and wherein the analysis of the one or more images is performed by using an automated system.

In an embodiment, the present invention provides a method of reliably detecting peripheral arterial disease in a subject comprising: a) administering Rb-82 chloride to a subject using an automated rubidium elution system controlled by software and hardware; b) scanning the lower extremities; c) using an expert system to score the peripheral arterial disease severity; and d) using decision support tools for clinical outcomes such as baseline score, survival rate after diagnosis and local disease progression rate; and a telemedicine portal for patient follow-up. The method further provides a quantifiable prediction tool based on flow rate measurements, serial imaging with repeated Rb-82 chloride injections and scanning method of lower extremities, which are independent of the scanner/camera type.

Figure 4:
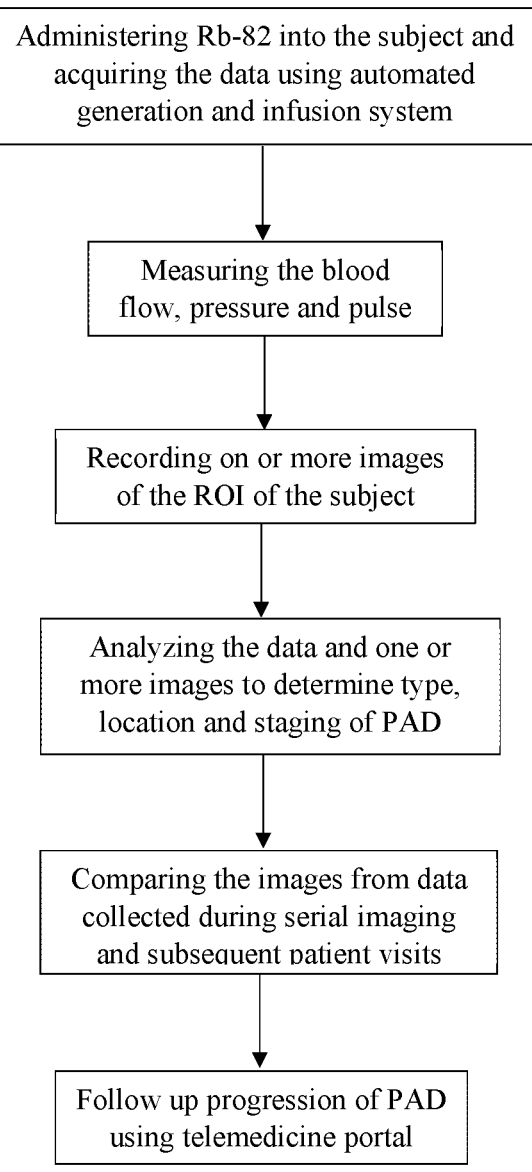
FIG. 4: Represents the flow diagram of a method of carrying out a non-invasive personalized screening test for the subjects suffering from peripheral arterial disease (PAD).

In an embodiment, the present invention provides a method of carrying out a non-invasive personalized screening test comprising: a) acquiring the data from the patient using automated generation and infusion system, preferably rubidium-82 generation and elution system; b) measuring the blood flow, pressure and pulse; c) recording an image of at least one body zone or region of interest of the subject; d) analyzing the data and image to determine type, location and staging of peripheral arterial disease; e) transmitting the data and the image to a secure databank; f) comparing the image from data collected during serial imaging and subsequent patient visits to adjust therapy and rehabilitation plans; and g) follow-up progression of peripheral arterial disease with patient using telemedicine portal. FIG. 4 represents the flow diagram of a method of carrying out a non-invasive personalized screening test.

In an embodiment, the present invention provides a reliable method of diagnostic testing during first line investigation to assess symptoms attributable to peripheral arterial disease in subjects with diabetes comprising: a) identify patients with a history suggesting narrowing or blockage of arteries requiring testing to elucidate the type and severity of peripheral arterial disease; b) scoring the peripheral arterial disease severity using an expert artificial intelligence engine to analyze the data and images received, and to score the peripheral arterial disease severity; c) generating a decision-support output report for review and validation by the interpreting physician; d) generating a peripheral arterial disease diagnosis report, prognosis and suggested peripheral arterial disease therapy report and/or consultation summary report to be sent back to the referring physician; and e) following-up rehabilitation using a wearable or non wearable telemedicine application.

In an embodiment, the present invention provides a method of determining whether a subject is suffering from a peripheral arterial disease comprising: a) administering into the subject a radionuclide and/or stress agent; b) performing one or more imaging scans of the subject; c) determining, by analysis of the one or more images, quantitative assessment of blood perfusion or flow in a region of interest in the subject; d) comparing the perfusion in the region of interest in the subject to a predetermined threshold value; and e) classifying the subject as having the peripheral arterial disease or as not having the peripheral arterial disease based on the comparison of step d); and thereby determining whether the subject is suffering with peripheral arterial disease or not.

Figure 5:
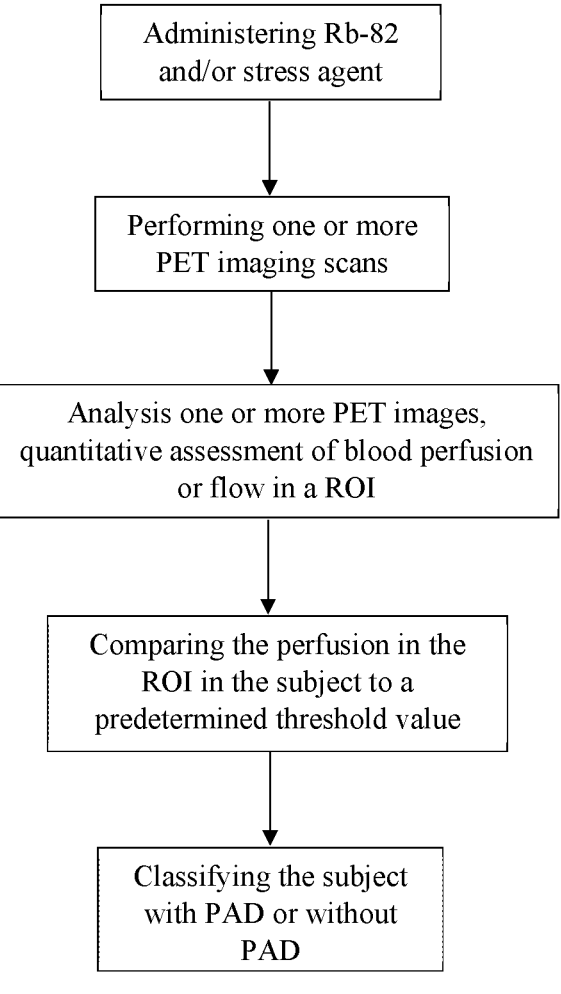
FIG. 5: Represents the flow diagram of a method of determining a subject suffering from peripheral arterial disease (PAD).

In an embodiment, the present invention provides a method of determining whether a subject is suffering with a peripheral arterial disease comprising: a) administering into the subject rubidium-82 and/or stress agent; b) performing one or more PET imaging scans of the subject; c) determining, by analysis of the one or more PET images, quantitative assessment of blood perfusion or flow in a region of interest in the subject; d) comparing the perfusion in the region of interest in the subject to a predetermined threshold value; and e) classifying the subject as having the peripheral arterial disease or as not having the peripheral arterial disease based on the comparison of step d); and thereby determining whether the subject is suffering with peripheral arterial disease or not. FIG. 5 represents the flow diagram of a method of determining a subject suffering from PAD.

In another embodiment, the present invention provides a method of preparing a report categorizing a subject as having a peripheral arterial disease or as not having a peripheral arterial disease comprising: a) receiving the data of one or more imaging scans of the subject performed by a imaging device after a radionuclide was administered into the subject; b) processing the data to determine blood perfusion for the region of interest in the subject and comparing the perfusion value to a predetermined threshold value; and c) populating a report categorizing the subject as having or not having peripheral arterial disease or at a risk of developing a peripheral arterial disease.

In another embodiment, a method of diagnosing a peripheral arterial disease in a subject suffering from diabetes mellitus comprises: a) calculating a dose of Rb-82 based on subject parameters, imaging system parameters, generation and/or infusion system parameters; b) administering the calculated dose of Rb-82 in a subject at rest and stress condition; c) image capturing by PET scanner; d) performing quantitative assessment of blood flow in lower extremities or limbs of the subject; e) performing image analysis and providing a severity score based on the assessment; f) performing diagnosis or identify the subjects at risk of developing peripheral arterial disease; and g) generating the report. The method further comprises a telemedicine portal for follow-up, therapy adjustment, rehabilitation of the subject. The method may further comprise a secure databank of subject parameters, images for Rb-82 dose calculation, image analysis, diagnosis and rehabilitation of subject.

The present invention further provides a method of treating a subject suffering with a peripheral arterial disease comprising: a) determining whether the subject is suffering from the peripheral arterial disease comprising: ((i) administering into the subject a radionuclide and/or a stress agent; (ii) performing one or more imaging scans of the subject; (iii) determining, by analysis of the one or more obtained images (iv) performing quantitative assessment of blood perfusion or flow; (v) comparing the perfusion value in the region of interest in the subject to a predetermined threshold value; and (vi) categorizing the subject as afflicted with the peripheral arterial disease when the perfusion value of the radionuclide in the subject is lower than the predetermined threshold value; and (b) treating the subject based on the determination obtained in step (a).

The present invention further provides a method of treating a subject suffering with a peripheral arterial disease comprising: (a) determining whether the subject is suffering with the peripheral arterial disease comprising: (i) administering into the subject rubidium-82 and/or a stress agent; (ii) performing one or more PET imaging scans of the subject; (iii) determining, by analysis of the one or more obtained PET images (iv) performing quantitative assessment of blood perfusion or flow; (v) comparing the perfusion value in the region of interest in the subject to a predetermined threshold value; and (vi) categorizing the subject as afflicted with the peripheral arterial disease when the perfusion value in the subject is lower than the predetermined threshold value; and (b) treating the subject based on the determination obtained in step (a).

In another embodiment, a method of treating a subject diagnosed with peripheral arterial disease or at risk of developing peripheral arterial disease comprises revascularization, cholesterol lowering medications, blood pressure control medications, blood sugar control medications, blood clot preventing medications, symptoms relieving medications, smoking cessation medications, surgery, amputation or life style management including but not limited to exercise, healthy diet, nutrition supplements or combinations thereof.

In an embodiment, the present invention provides accurate quantitative assessment of the peripheral arterial disease based on blood perfusion to the affected body part.

In an embodiment, the subject is a human subject.

In an embodiment, the human subject is a male or female subject.

In an embodiment, the subject can be suffering from additional disease like metabolic disease.

In an embodiment, the additional disease is diabetes mellitus.

In an embodiment, the PET radionuclide is introduced by injection or infusion into the bloodstream of the subject. In a preferred embodiment, radionuclide is administered via automated generation and/or infusion system.

In an embodiment, radionuclide generator is selected from $^{99}$Mo/$^{99m}$Tc, $^{90}$Sr/$^{90}$Y, $^{82}$Sr/$^{82}$Rb, $^{188}$W/$^{188}$Re, $^{68}$Ge/$^{68}$Ga, $^{42}$Ar/$^{42}$K, $^{44}$Ti/$^{44}$Sc, $^{52}$Fe/$^{52m}$Mn, $^{72}$Se/$^{72}$As, $^{83}$Rb/$^{83m}$Kr; $^{103}$Pd/$^{103m}$Rh, $^{109}$Cd/$^{109m}$Ag, $^{113}$Sn/$^{113m}$J. $^{113m}$In, $^{118}$Te/$^{118}$Sb, $^{132}$Te/$^{132}$I, $^{137}$Cs/$^{137m}$Ba, $^{140}$Ba/$^{140}$La, $^{134}$Ce/$^{134}$La, $^{144}$Ce/$^{144}$Pr, $^{140}$Nd/$^{140}$Pr, $^{166}$Dy/$^{166}$Ho, $^{167}$Tm/$^{167m}$Er $^{172}$Hf/$^{172}$Lu, $^{178}$W/$^{178}$Ta, $^{191}$Os/$^{191m}$Ir, $^{194}$Os/$^{194}$Ir, $^{226}$Ra/$^{222}$Rn and $^{225}$Ac/$^{213}$Bi.

As used herein, the term "column" refers to the functional component of a radiopharmaceutical generator, wherein a hollow column made up of a radiation resistant material is packed with an ion exchange resin, wherein the ion exchange resin is loaded or charged with parent radioisotope. The ion exchange resin has higher affinity for parent radioisotope as compared to daughter radioisotope. Thus, on elution with a suitable medium, daughter radioisotope is eluted from the generator while parent radioisotope stays adsorbed to matrix of ion exchange resin. The daughter radioisotope is formed in-situ by radioactive decay of parent radioisotope in the column.

In an embodiment, pharmaceutical compositions are provided comprising imaging agent. The composition can comprise radionuclide or radionuclide labelled to ligand and/or one or more excipient. In another embodiment, the ligand can be labelled or unlabeled. In additional embodiment, the radionuclide for administration to the subject comprising Rb-82 generated by automated generation and infusion system comprising on-board strontium rubidium generator. The system automatically pumps the eluant from the source into the generator or column comprising bound Sr-82 and elutes Rb-82 in a form of $^{82}$Rb—Cl, which is then infused/administered into patient after activity measurements. In other embodiments, the imaging agent having a longer half-life can be produced at other location and can be placed as a bulk solution in automated infusion system for administering into a subject with or without further dilution. In still another embodiment, the imaging agent can be prepared in a radiopharmacy or manufacturing location and can be transported to the administration location or diagnostic center or hospital in a suitable container like syringes, vials, ampoules, pre-filled syringes. The composition can be presented in a kit comprising one or more containers with radionuclide in a shielded container. The pharmaceutical compositions of the present invention can be in the form of lyophilized powder, liquids, and suspensions.

In an embodiment, the present invention provides a method of diagnosing a peripheral arterial disease in a subject suffering from diabetes mellitus with a closed loop generation and/or infusion system comprises:

a) calculating a dose of Rb-82 based on subject parameters, imaging system parameters, generation and/or infusion system parameters;

b) administering the calculated dose of Rb-82 in a subject at rest and stress condition;

c) image capturing by PET scanner;

d) performing quantitative assessment of blood flow in lower extremities or limbs of the subject;

e) analyzing one or more images and providing a severity score based on the assessment and presented in a numerical or percentage value of occluded or affected tissue;

f) performing diagnosis or identify the subjects at risk of developing peripheral arterial disease; and g) generating the report;

wherein the closed loop generation and/or infusion system comprises: a radionuclide generator, an activity detector, a controller, a dose calibrator, a pump, eluant source and an automated elution system controlled by software and hardware for generation and infusion of a radionuclide.

In an embodiment, the present invention provides the closed loop generation and/or infusion system, wherein the subject suffering from or at a risk of developing peripheral arterial disease is diagnosed and/or treated comprising administering a dose of Rb-82 using a closed loop Rb-82 elution system and performing a quantitative assessment of blood flow to the region of interest.

In an embodiment, the automated generation and infusion system is a rubidium (Rb-82) elution system, comprises the components described in FIG. 1. In an embodiment, the elution system comprises reservoir 4 of sterile saline solution (e.g. 0.9% Sodium Chloride Injection); a pump 6 for drawing saline from the reservoir 4 through the supply line 5 and the generator line (between 30 and 22) at a desired flow rate; a generator valve 16 for proportioning the saline flow between a strontium-rubidium ($^{82}$Sr/$^{82}$Rb) generator 8 and a bypass line 18 which circumvents the generator 8; a positron detector 20 located downstream of the merge point 22 at which the generator and bypass flows merge; and a patient valve 24 for controlling supply of active saline to a patient outlet 10 and a waste reservoir 26. A controller 28 is preferably connected to the pump 6, positron detector 20 and valves 16 and 24 to control the elution system 14 in accordance with a desired control algorithm.

Figure 2:
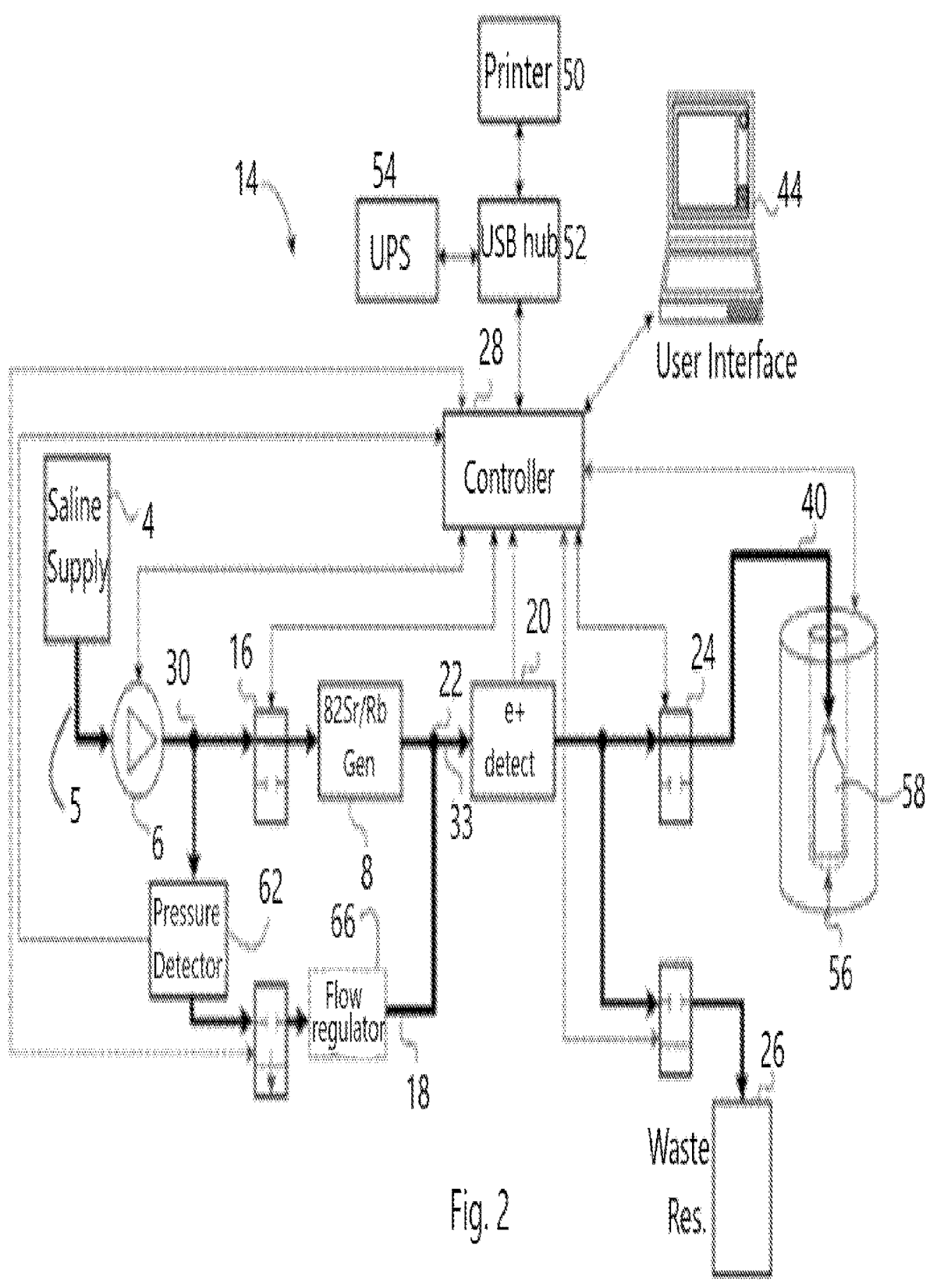
FIG. 2: Depicts a block diagram schematically demonstrating key elements of an automated Rb-82 generation and infusion system in accordance with another embodiment of the present invention.

FIG. 2 depicts a block diagram schematically illustrating principal elements of a rubidium elution system in accordance with another embodiment of the present invention. The rubidium elution system of FIG. 2 has similar elements as the Rubidium elution system of FIG. 1, and additional elements. These additional elements preferably include one or more of a printer 50 and USB (Universal Serial Bus; or other communications port) port 52, a pressure detector 62, a dose calibrator 56, a flow regulator 66, or a UPS (Uninterruptible Power Supply) 54.

The rubidium elution system of FIG. 2 can be used to assess various aspects of the system, such as a concentration of $^{82}$Rb, $^{82}$Sr, or $^{85}$Sr in a fluid that is eluted from the generator, the volume of the fluid that is eluted from the generator, or the pressure of the fluid flowing through at least one portion of the system. Information about these aspects of the system can be gathered by various elements of the system, and sent to the controller. The controller and/or user interface computer (which can comprise a processor and memory) can analyze this gathered data to assess the state of the system.

The rubidium elution system of FIG. 2 can additionally have a dose calibrator 56. The dose calibrator 56 can be used instead of a patient outlet, or in addition to a patient outlet, along with a valve that can be configured to direct fluid to the patient outlet or to the dose calibrator. The dose calibrator 56 comprise a vial 58 (such as a 50 mL vial) that collects the fluid as it otherwise exits the elution system. The dose calibrator 56 can be communicatively coupled to the controller, and configured to send information to the controller, such as an activity concentration of $^{82}$Rb, $^{82}$Sr, or $^{85}$Sr in a fluid that is eluted from the generator. The dose calibrator 56 can include a radioactivity shielding material.

In an alternate embodiment according to the present invention, the automated generation and infusion system is embodied in a portable (or mobile) cart that house some or all of the generator, the processor, the pump, the memory, the patient line, the bypass line, the positron detector, and/or the calibrator, sensors, dose calibrator, activity detector, waste bottle, controller, display, and computer. The cart carrying the components for radioisotope generation and infusion is mobile and can be transferred from one place to another to the patient location or centers, hospitals as required.

In an embodiment, the method of diagnosing/imaging a region of interest of a subject comprising: a) input one or more subject parameters selected from weight, age, height, mass and sex into the rubidium elution system; b) automatically calculating the appropriate dose of rubidium-82 based on one or more subject parameters; c) generating a dose of Rb-82 from rubidium elution system; d) administering Rb-82 and/or stress agent to the subject in need thereof; e) performing PET scanning of the region of interest; f) automated analysis of the images by computerized software; g) quantitative assessment of the blood flow in the region of interest; h) generating automated report of the assessment; and i) providing most appropriate therapy options for the subject.

In an embodiment, all in one system for diagnosis and/or treatment of peripheral arterial disease comprises; the hardware apparatus comprises of Rb-82 generator, injection delivery, elution system and touchscreen computer with real-time graphical user interface for viewing delivery pattern of tracer, the software accurately measures and delivers the required dose volume within specified time; the software includes data acquisition, control, imaging, reporting, artificial intelligence engine and expert system, and telemedicine modules; the software includes an engineering model, based on whole body movements, blood flow, fat, muscle and bone as well as capturing a single joint; multi-joints, and a combination of joints; the software includes the biomechanical extremity model, including anatomic segments, bony landmarks, joint motion and coordinates, number of markers, and muscle tissue. The All-in-One Apparatus is positioned near subject.

In another embodiment of the present invention, preliminary investigation at patient intake comprises; the software will capture patient pre-screening historical data, symptoms and risk factors suggestive of peripheral arterial disease including demographic information, previous serial imaging results, physician referrals, patient weakness and pain in lower extremities, patient fatigue, smoking, diabetes, dyslipidemia, blood sample history, comorbid conditions, height, weight, body mass index, waist and hip circumferences, cardiovascular risk factors, claudication pain history, acquired brain injury, list of current medications and inflammation; patient screening data will be used as input to the model.

In another embodiment of the present invention, a software data acquisition DAQ module with apparatus is provided. The software includes graphing dose delivery in real-time with offset adjustments; input curve flagging when to scanning; the software includes acquisition protocol; quantitative blood flow measurement; acquisition adjustment; saline push to optimize image quality after elution; measurement of patient pulse and blood pressure in lower extremities abnormal movement, compression, or abnormal flow.

In another embodiment of the present invention, features of imaging module are provided comprising; administering personalized single "rest" Rb-82 chloride dose protocol and start imaging; administering a pharmacologic stress agent and second dose protocol after resting dose infusion; scanning; software based time correction factors/noise offsets to improve image quality; software based correction factors to allow imaging protocol independent of the scanner/camera type; the protocol provides improved granularity of abnormal images; measuring of relative image changes over time to report on peripheral arterial disease progression.

In another embodiment of the present invention, a scoring module is provided comprising; a software to provide an expert system module to score the severity of peripheral arterial disease based on imaging results; expert system to include initial baseline score and flow rate score prediction tool.

In an embodiment of the present invention, diagnosis reporting module is provided comprising; assessment checklist summary report, including rest/stress flow reserve; suggested diagnostic report to be validated through electronic signature by physician within software; prediction factors for muscle necrosis in lower extremities; prediction tool for probability of amputation based on serial imaging and blood flow rate measurements.

In an embodiment of the present invention, suggested treatment module is provided comprising; a treatment plan based on artificial intelligence engine, input from detailed serial imaging and blood flow intervals; treatment report to be validated through electronic signature by physician within software. In an embodiment of the present invention, follow-up telemedicine module is provided comprising: software will link to a patient with a wearable or non wearable device to capture data from patient after diagnosis including software application to provide a telemedicine application to track patient aerobic exercise, blood pressure and mental health; software can include patient learning module to support rehabilitation; software user interface will provide option for physician to communicate and track patient progress; clinical outcome report to measure and track effects of aerobic exercise to peripheral arterial disease severity during rehabilitation and adapt levels based on serial imaging; link to other specialists for patient follow-up during peripheral arterial disease rehabilitation including occupational therapy/physical therapy/psychologist.

In an embodiment, the assessment is based on lower extremities perfusion at rest, along with perfusion reserve in response to pharmacological stress or exercise induced stress. In an embodiment, the assessment can be qualitative or quantitative.

In an embodiment, the predetermined radionuclide uptake potential or blood flow or perfusion threshold value is calculated. The threshold value is calculated in comparison to the occluded tissues to normal tissues or unoccluded tissues.

In an embodiment, the analysis of the one or more images is performed by computerized analysis.

In an embodiment, the analysis of the one or more images is performed on computerized algorithms based on artificial intelligence, machine learning or artificial neural network or simulated neural network (SNN) and/or deep learning.

In some embodiments, diagnosis of peripheral arterial disease further comprises carrying out one or more computed tomography (CT) scans of the subject.

In some embodiments, diagnosis of peripheral arterial disease further comprises carrying out one or more magnetic resonance imaging (MRI) scans of the subject.

In another embodiment, the present invention provides a method of determining whether a subject is at risk for developing a peripheral arterial disease or not.

The present invention provides a method of determining whether a subject is at risk of developing a peripheral arterial disease comprising: a) administering into the subject a rubidium-82 radionuclide and/or stress agent; b) performing one or more PET imaging scans of the subject; c) determining, by analysis of the one or more images, blood perfusion or flow in the region of interest; d) performing quantitative assessment of blood perfusion or flow to a predetermined threshold value; and e) categorizing the subject as at risk for developing the peripheral arterial disease or as not at risk for developing the peripheral arterial disease based on the comparison of step d) thereby determining whether the subject is at risk for developing the peripheral arterial disease or not.

In some embodiments, the predetermined threshold value is determined by analyzing a control subject or group of control subjects that are not suffering with a peripheral arterial disease and/or diabetes mellitus.

In an embodiment, image analysis, the assessment of blood flow in the region of interest and/or treatment suggestions can be provided by computerized software, preferably artificial intelligence based algorithms.

In the present application, all numbers disclosed herein can vary by 1 percent, 2 percent, 5 percent, or up to 20 percent if the word "about" is used in connection therewith. This variation can be applied to all numbers disclosed herein.

Each embodiment disclosed herein is contemplated as being applicable to each of the other disclosed embodiments. Thus, all combinations of the various elements described herein are within the scope of the invention.

This invention will be better understood by reference to the example, which follow, but those skilled in the art will readily appreciate that the specific experiments detailed are only illustrative of the invention as described more fully in the claims which follow thereafter.

EXAMPLE

Figure 3:
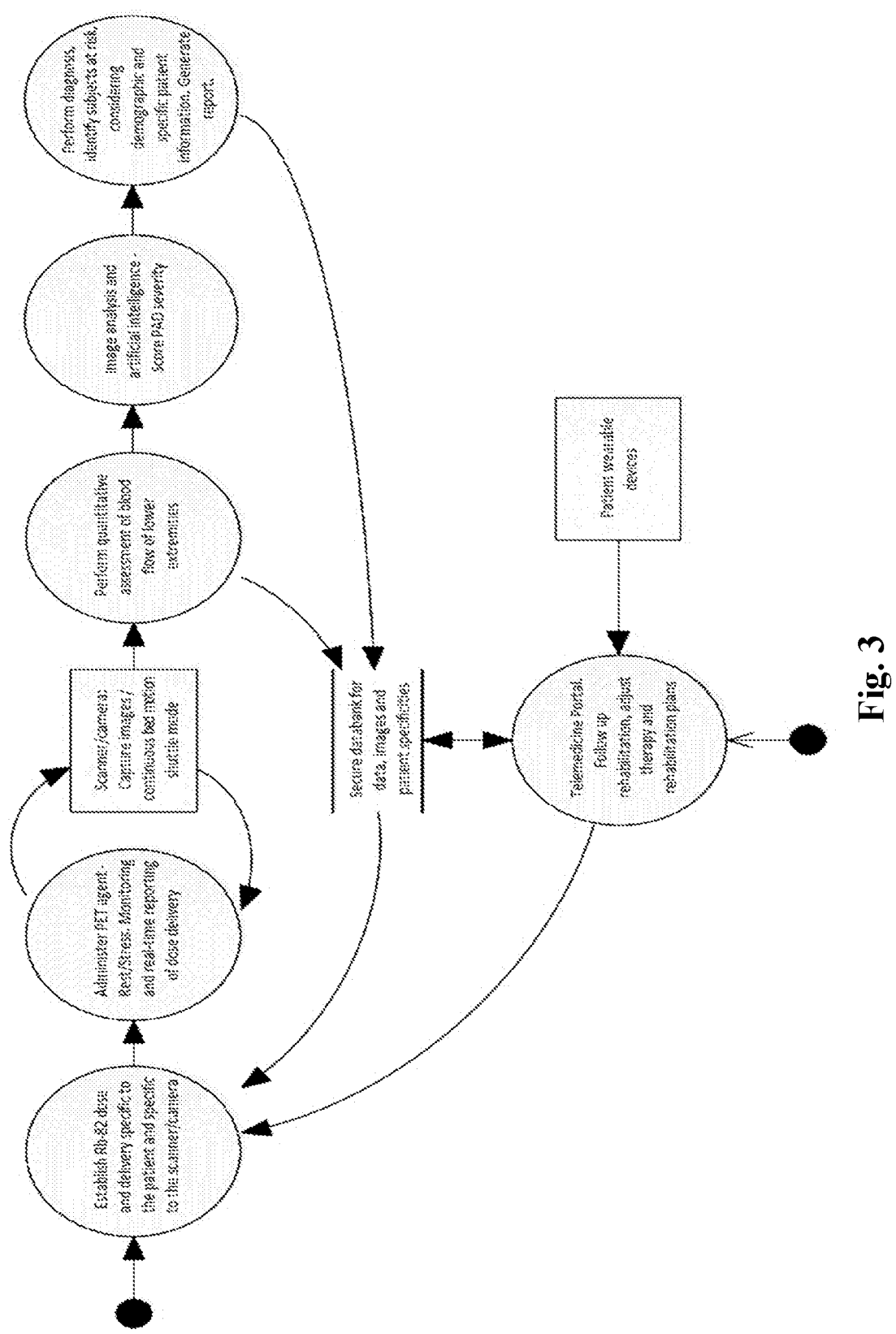
FIG. 3: Depicts a flow chart of the process of radionuclide administration, imaging, assessment, diagnosis and telemedicine.

In these experiments, $^{82}$Rb—Cl was generated using automated generation and infusion system having on-board Sr—Rb generator. Appropriate dose of $^{82}$Rb was calculated by the system. After dose calculation, the system automatically instructs the controller to pump eluant (sodium chloride) from the eluant source and generate a calculated dose of Rb-82, which is administered to a subject via infusion system. Imaging scans were performed using the imaging system. Similarly, images were obtained after administering stress agent into the subject. Qualitative and quantitative assessment was performed by computerized software depending on the blood perfusion in the region of interest and severity score is provided for each subject. Based on the assessment, if the subject is found suffering from peripheral arterial disease or at risk of developing a peripheral arterial disease, suitable therapy options are provided (FIG. 3). The method can also be carried out as represented in FIG. 4 and FIG. 5.

What is claimed:

1. A closed loop generation and/or infusion system comprising a radionuclide generator, an activity detector, a controller, a dose calibrator, a pump, eluant source and an automated elution system controlled by software and hardware for generation and infusion of a radionuclide for administering a dose of generated radionuclide into a subject for diagnosing a peripheral arterial disease in a subject suffering from or suspected of suffering from peripheral arterial disease and/or metabolic disease by performing quantitative assessment of blood flow in lower extremities or limbs of the subject;

wherein the quantitative assessment is performed by analyzing one or more images and providing a severity score;

wherein the analysis of the one or more images is performed by using an automated system;

wherein the closed loop generation and/or infusion system further comprises:

a) calculating a dose of Rb-82 based on subject parameters, imaging system parameters, generation and/or infusion system parameters;

b) administering the calculated dose of Rb-82 in a subject at rest and stress condition;

c) image capturing by PET scanner;

d) performing quantitative assessment of blood flow in lower extremities or limbs of the subject;

e) analyzing one or more images and providing a severity score based on the assessment and presented in a numerical or percentage value of occluded or affected tissue;

f) performing diagnosis or identify the subjects at risk of developing peripheral arterial disease; and g) generating the report, wherein the dose of radionuclide ranges from 0.01 milli-Becquerel to 10,000 milli-Becquerel.

2. The closed loop generation and/or infusion system according to claim 1, wherein the generation comprises elution of daughter isotope from parent isotope bound to generator column by suitable eluant.

3. The closed loop generation and/or infusion system according to claim 2, wherein the parent isotope comprises Sr-82 and daughter isotope comprises Rb-82.

4. The closed loop generation and/or infusion system according to claim 2, wherein the elution mode is selected from group consisting of constant activity, constant flow, constant pressure, constant infusion time and constant dose or combination thereof.

5. The closed loop generation and/or infusion system according to claim 1, wherein the radionuclide generator comprises a $^{82}$Sr/$^{82}$Rb generator.

6. The closed loop generation and/or infusion system according to claim 1, wherein the system is automated.

7. The closed loop generation and/or infusion system according to claim 1, wherein the dose of radionuclide is calculated automatically based on subject parameters, radionuclide generation and infusion system parameters, and imaging system parameters.

8. The closed loop generation and/or infusion system according to claim 7, wherein the subject parameters comprise subject weight, height, sex, age, ongoing medications, allergies, radiation sensitivity, surface area, body mass, kidney and liver function status or combination thereof.

9. The closed loop generation and/or infusion system according to claim 7, wherein the radionuclide generation and infusion system parameters comprises type of radionuclide, generator type, generator age, flow rate, activity to be administered, infusion time, dose, activity detector calibration, parent isotope breakthrough.

10. The closed loop generation and/or infusion system according to claim 7, wherein the imaging system parameters comprise scanner resolution, scanner sensitivity and type of camera.

11. The closed loop elution system according to claim 7, wherein the dose is fixed dosing or linear dosing based on subject weight.

12. The closed loop elution system according to claim 1, wherein the system is communicatively or electronically coupled to imaging system.

13. The closed loop generation and/or infusion system according to claim 12, wherein the imaging system comprises PET or SPECT imaging systems.

14. The closed loop generation and/or infusion system according to claim 1, wherein the metabolic disease is diabetes mellitus.

15. The closed loop generation and/or infusion system according to claim 1, wherein the peripheral arterial disease comprises limb ischemia.

16. The closed loop generation and/or infusion system according to claim 1, wherein the subject suffering from or at a risk of developing peripheral arterial disease is diagnosed and/or treated comprising administering a dose of Rb-82 using a closed loop Rb-82 elution system and performing a quantitative assessment of blood flow to the region of interest.

17. The closed loop generation and/or infusion system according to claim 1, wherein the system further comprises a secure databank of subject parameters, images for Rb-82 dose calculation, image analysis, diagnosis and rehabilitation of subject.

18. A method of diagnosing a peripheral arterial disease in a subject suffering from diabetes mellitus with a closed loop generation and/or infusion system comprises:

a) calculating a dose of Rb-82 based on subject parameters, imaging system parameters, generation and/or infusion system parameters, wherein the dose of radionuclide ranges from 0.01 milli-Becquerel to 10,000 milli-Becquerel;

b) administering the calculated dose of Rb-82 in a subject at rest and stress condition;

c) image capturing by PET scanner;

d) performing quantitative assessment of blood flow in lower extremities or limbs of the subject;

e) analyzing one or more images and providing a severity score based on the assessment and presented in a numerical or percentage value of occluded or affected tissue;

f) performing diagnosis or identify the subjects at risk of developing peripheral arterial disease; and g) generating the report; wherein the closed loop generation and/or infusion system comprises: a radionuclide generator, an activity detector, a controller, a dose calibrator, a pump, eluant source and an automated elution system controlled by software and hardware for generation and infusion of a radionuclide.

\* \* \* \* \*